(12) United States Patent
Brumer et al.

(10) Patent No.: US 8,866,592 B2
(45) Date of Patent: Oct. 21, 2014

(54) METHOD FOR DETECTING AND COMMUNICATING WITH RFID MEMORY DEVICES

(71) Applicant: Covidien LP, Mansfield, MA (US)

(72) Inventors: Rebecca Brumer, Arlington, MA (US); Nassib G. Chamoun, Needham, MA (US); Rafael M. Cordero, Bedford, MA (US); Marc Davidson, Andover, MA (US); James P. Kiely, Belmont, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/937,108

(22) Filed: Jul. 8, 2013

(65) Prior Publication Data

US 2013/0293357 A1 Nov. 7, 2013

Related U.S. Application Data

(63) Continuation of application No. 11/871,599, filed on Oct. 12, 2007, now Pat. No. 8,482,385.

(60) Provisional application No. 60/851,437, filed on Oct. 13, 2006.

(51) Int. Cl.
*H04Q 5/22* (2006.01)
*G08B 26/00* (2006.01)
*G05B 11/01* (2006.01)
*G06K 19/00* (2006.01)
*G06K 19/06* (2006.01)

(52) U.S. Cl.
USPC ....... 340/10.1; 340/505; 340/12.51; 235/492; 235/487

(58) Field of Classification Search
None
See application file for complete search history.

(56) References Cited

U.S. PATENT DOCUMENTS

| 6,298,255 | B1 | 10/2001 | Cordero et al. |
| 7,213,766 | B2 * | 5/2007 | Ryan et al. ............ 235/492 |
| 7,273,173 | B2 | 9/2007 | Forster |
| 7,277,016 | B2 | 10/2007 | Moskowitz et al. |
| 7,526,791 | B2 | 4/2009 | Wong et al. |

(Continued)

FOREIGN PATENT DOCUMENTS

| JP | 2006268279 A | 10/2006 |
| WO | 00/39741 A1 | 7/2000 |
| WO | WO-2004079647 A | 9/2004 |
| WO | 2005/020135 A1 | 3/2005 |

OTHER PUBLICATIONS

International Search Report issued for PCT/US07/081241, dated May 30, 2008, 3 pages.

(Continued)

*Primary Examiner* — Jennifer Mehmood
*Assistant Examiner* — Pameshanand Mahase
(74) *Attorney, Agent, or Firm* — Shvarts & Leiz LLP

(57) ABSTRACT

This invention relates to a system of communicating with a radio frequency identification (RFID) transponder microchip (IC) for the purpose of accessing pre-programmed data. Such system involves direct electrical contact between the system reading the data from the memory in the transponder IC and the IC itself via two mechanical contact points. This system provides an interface with a transponder IC in order to energize the IC. Once the presence of the transponder IC is detected, the host system can read or write to and process preprogrammed data stored in the IC.

21 Claims, 5 Drawing Sheets

(56) References Cited

U.S. PATENT DOCUMENTS

| | | |
|---|---|---|
| 2004/0008123 A1* | 1/2004 | Carrender et al. ....... 340/825.49 |
| 2005/0001712 A1 | 1/2005 | Yarbrough |
| 2005/0019213 A1 | 1/2005 | Kechagia et al. |
| 2005/0104719 A1 | 5/2005 | Ramamurthy et al. |
| 2005/0142033 A1 | 6/2005 | Glezer et al. |
| 2005/0211784 A1* | 9/2005 | Justin ........................ 235/492 |
| 2005/0258242 A1 | 11/2005 | Zarembo |
| 2005/0280511 A1 | 12/2005 | Yokoyama et al. |
| 2005/0289083 A1 | 12/2005 | Ngai et al. |
| 2006/0061475 A1 | 3/2006 | Moskowitz et al. |
| 2006/0255941 A1 | 11/2006 | Carrender et al. |
| 2007/0018832 A1 | 1/2007 | Beigel et al. |
| 2007/0046471 A1 | 3/2007 | Nyalamadugu |
| 2007/0164868 A1 | 7/2007 | Deavours et al. |
| 2007/0270672 A1 | 11/2007 | Hayter |

OTHER PUBLICATIONS

International Search Report issued for PCT/US07/081249, dated May 28, 2008, 4 pages.

Communication Pursuant to Article 94(3) EPC issued by the European Patent Office in connection with counterpart European Patent Application No. 07 868 435.4, dated Apr. 24, 2013, 7 pages.

* cited by examiner

METHOD FOR DETECTING AND COMMUNICATING WITH RFID MEMORY DEVICES

This application is a continuation of U.S. patent application Ser. No. 11/871,599, filed Oct. 12, 2007, now U.S. Pat. No. 8,482,385, which claims priority to U.S. Provisional Application No. 60/851,437, filed Oct. 13, 2006, both of which are incorporated herein by reference in their entireties.

BACKGROUND OF THE INVENTION

In many applications the benefit of using Radio Frequency Identification (RFID) as a means for a host system to communicate with external components is that it does not require direct contact or even line of sight in order to communicate data. However, in certain applications, there also exist several benefits to utilizing RFID hardware and protocols in the manner of direct contact rather than by generation and modulation of an RF field Applications wherein contact smart modules are used as a means to store data are very common. Secure credit cards often have a smart module mounted onto the surface of the card. When the card is inserted into a receiver terminal, a set of probes or pins make contact with each of the contacts on the smart module. The data on the smart module memory device is read and processed by a system inside the receiver terminal.

In U.S. Pat. No. 6,298,255, a memory device in the form of a 6-contact smart card memory module is incorporated into an electrophysiological sensor system allowing for the automatic authentication and configuration of the sensor. The smart card memory module contains various data to identify the source of the sensor as well as data regarding the status of the sensor. A biopotential signal monitor and accompanying hardware and software interface read and process the data on the memory module. In this invention, the memory device is located on a rigid substrate that inserts into a mating receptacle. The mating receptacle on the cable contains a 6 pin connector that must align correctly in order to interface with and thus read the data contained by the smart module. A ground guard is used to provide patient protection in the event of a circuit fault. This device does not use RFID memory devices.

In US Patent US2006/0255941 A1, Carrender et al. describe a method by which an RFID chip mounted on a recessed flexibly substrate with contacts (strap) can be functionally tested for performance parameters. The method involves directly coupling paired test elements to the paired contacts on an RFID strap and then transmitting test signals to the chip and return signals from the chip. Test data from the chip is transmitted in the return signals, which may include a manufacturer code or a pre-programmed test code. This method provides feedback on the functionality of the RFID assembly.

In U.S. Pat. No. 7,273,173 Forster et al. describes a RFID device detection system which used both antenna and contact coupling on an RFID transponder—in this patent, the passive RFID device receives power and communicates via conductive transmission lines in an antennaless system. The coupling between the transponder and the reader uses either short range electric field or magnetic field coupling.

In U.S. Pat. No. 7,277,016, Moskowitz et al. describe several means by which RFID tags can be disabled for the purpose of providing an extra layer of security for the data. It is suggested that once an RFID tag is disabled by way of damaging the antenna, that the short antenna stubs may be electrically contacted by mechanical probes thus allowing the tag to be read once via direct contact. However, the method by which this can be achieved is not presented nor discussed in this patent publication.

In US Patent 2004/0008123A1, Carrender et al. describe a system for monitoring pharmaceuticals that uses an RFID tag mounted in the cap of a tablet container which stores various information relating to the pharmaceuticals, such as data about the manufacture, distribution and sale thereof. The RFID tag is also fitted with capacitive sensors that sense the position of the tablet container cap. A standard RFID reader is used to wirelessly read the data from the RFID tag.

As with contact smart card memory module described above, there is also a commercially available product, dual interface ICs which incorporate multi-functional chips for applications where a card may need to be read by a contact or a contactless system. For example, an SLE66CL80PE(M) (Infineon Corporation) features ISO/IEC 14443 Type B (RFID protocol) contactless interfaces as well as an ISO/IEC 7816 contact-based interface, on a single chip. In direct contact mode, the contact-based interface is used while when wireless communication is required, the contactless interface is engaged. The contactless protocol is not used when the card is read in direct contact mode.

SUMMARY OF THE INVENTION

This invention relates to a system in which data stored on a memory device incorporated within a connectable portion of a system can be accessed using RFID hardware and protocols without the complexity of generating and communicating via an RF field. In this invention, the connectable portion of the system is comprised of an RFID transponder IC without an antenna, which is placed directly on a carrier substrate and is powered by two-wire direct contact. An RFID transponder IC can be described as a passive device that is activated by receiving power. Generally this is in the form of an RF electrical field that is generated in the antenna loops. Alternately, power and communication to the RFID transponder may be provided directly by current through transmission lines from a host system. In this context, the primary host system is defined as the system in which data from the connectable portion is read, interpreted and processed. The communication protocol and exchange of signal in this arrangement will emulate that which occurs through a standard RFID air interface. This invention has the advantage of obviating the need for both antennae and furthering the cost advantages of an RFID-based system.

This primary host system is comprised, in its most basic form, of an RFID interrogator chip and antenna matching circuits. It may also include a power source such as a battery and a microprocessor for controlling the interrogator chip or for processing read data. The components of the primary host system may be physically located in a larger system such as a monitoring system or may be embedded in an interface cable that connects the primary host system to the connectable portion.

One application of the RFID transponder IC in a contact configuration is to contain product data about a single use disposable medical device while the interrogator IC and matching circuits are found in the interface cable that connects the disposable device to the host system. When the device is connected to the host system via the cable, the presence of the device is detected by achieving and completing communication or by a change in circuit voltage between the interrogator IC and the transponder IC. After detection of the device by the interrogator, power is provided to the passive transponder IC and it transmits the pre-programmed data to the host monitoring system. This data may include device information pertaining to its manufacture and validity for use (e.g. expiration date, previous number of uses, etc.) so that the host system may authenticate the device and determine whether it meets the necessary criteria for use. Disconnection of the connectable portion containing the RFID chip is detected by the primary host system in the same manner that a connection was detected. Monitoring of connections and disconnections is performed continuously.

In alternate embodiments of this invention various types of data may be contained in the connectable portion, as appropriate to each unique application. This system may be used in numerous applications. Such applications include as an identification and authentication system for inventory control, patient drug management, or item authentication.

DETAILED DESCRIPTION OF THE PREFERRED EMBODIMENTS

Figure 1A:
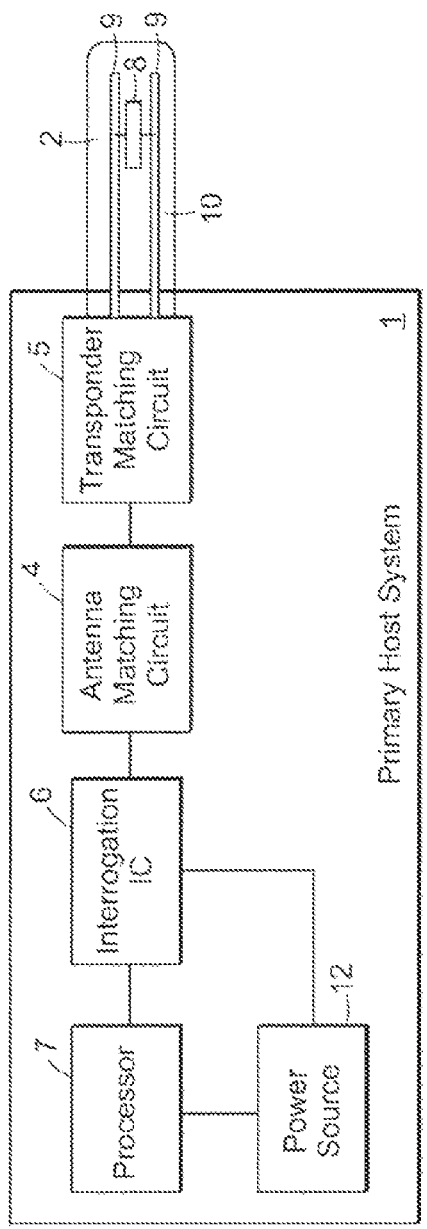
FIG. 1a illustrates the overall system of the present invention, including Primary Host System and Connectable Portion.
Figure 1B:
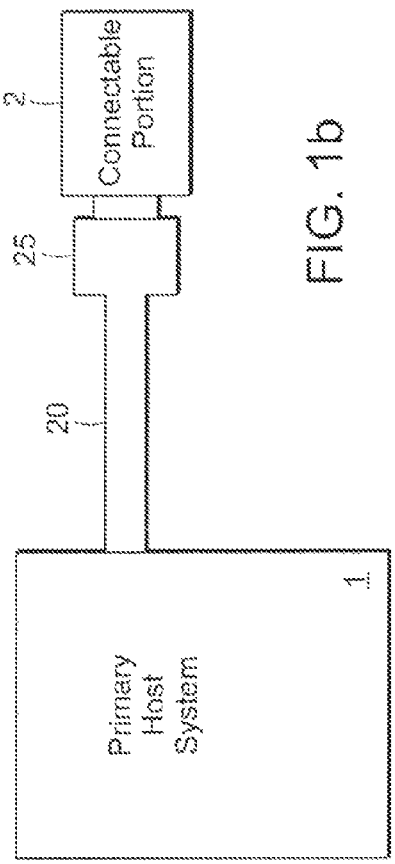
FIG. 1b illustrates an alternate embodiment of the overall system that includes an interface cable.

The present invention comprises a monitoring system that includes a primary host portion 1 and a connectable portion or carrier 2, as illustrated in FIG. 1. Such connectable portion 2 of the system may be a sensing or monitoring device. The primary host portion is a system that comprises of an interrogator function and a data collection and processing function. The connectable (disconnectable) portion of the system incorporates an RFID device used to store information, typically about the device being connected. It may also incorporate a data acquisition means such as a sensor. Upon the connection of the connectable portion 2 to the primary host system via an interface cable or receptacle, such connection will be detected and the data on the RFID device will be read by the primary host system. Such primary host system comprises of an interrogator chip 3 which may be embedded in an interface cable 20 or mounted in the system hardware, a source of supporting electrical power for the circuitry and a processor chip to process the data. Data transmission between the interrogator chip in the primary host system (possibly via an interface cable) and the transponder microchip on the connectable portion requires only two contact points. The primary host system will also detect a disconnection upon removal of the connectable portion 2 from its interface cable or receptacle. FIG. 1b illustrates an alternate construction of the system in which the connectable portion 2 is connected to the primary host system 1 by an interface cable 20. The interface cable 20 is connected to the connectable portion by a connector 25, which may contain the interrogator chip 3.

The present invention generally provides a system for emulating over the air power transmission and data communication. This is achieved by interrogating the RFID transponder IC 8 on the connectable portion 2 via direct contact for the purpose of reading and/or updating pre-programmed data stored in its memory. The primary host system 1 which enacts this method of communication is comprised of: an RFID interrogator IC 3, electronic components for an antenna matching circuit 4 and a transponder matching circuit 5. The system may or may not include an additional microprocessor 7 to facilitate communication between the RFID IC and the host system and to handle data collection and processing. The system may or may not include a battery or other form of portable power source 12 to provide power to the interrogator IC 3. The voltage provided by the power source is dependent on the specifications of the interrogator IC 3.

Within the connectable portion 2, a RFID transponder IC 8 is mounted on a two conductive contacts 9 which are located on a non-conductive substrate 10. Such substrate 10 may be any number of non-conductive materials such as a polyester sheet or film, a printed circuit board, or a molded plastic surface. In an alternate embodiment the transponder IC 8 is first mounted on a conductive strap which in turn is mounted to two conductive contacts 9 which are located on a non-conductive substrate. The 2 physical conductive points on the transponder IC 8 are coupled to wires which terminate at a connector. Alternately, the conductive points are coupled to conductive ink traces which terminate at a connector. Such conductive ink traces may be printed on the substrate 10 or may be deposited by various means well known in the art.

Figure 2:
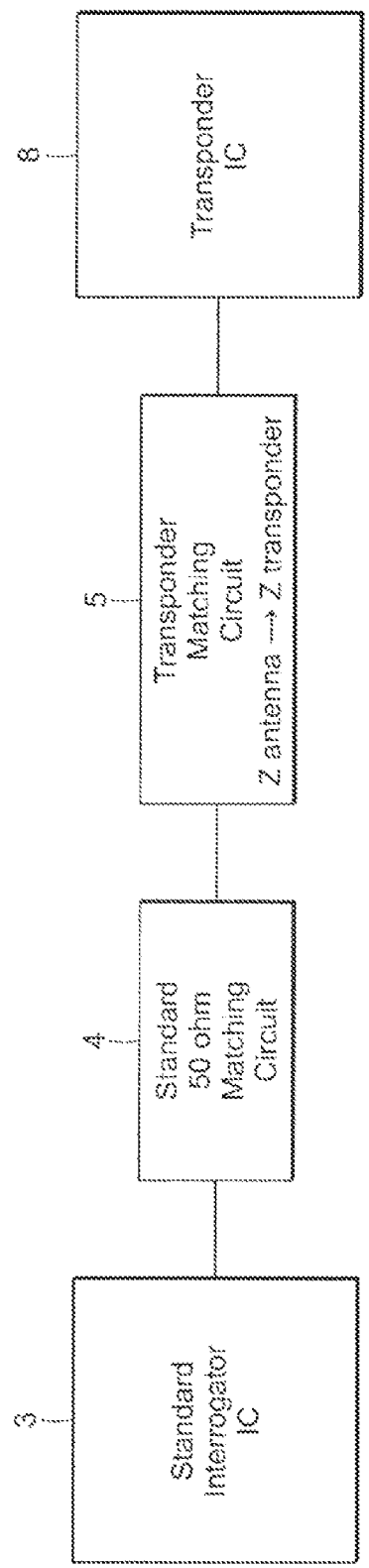
FIG. 2 illustrates the physical connections within the communication system.

One embodiment of the invention is shown in block diagram form in FIG. 2. In this embodiment, a standard HF (high frequency) RFID interrogator chip 3 is used along with its standard antenna matching circuit 4 designed for connection to a 50 ohm antenna. This antenna matching circuit 4 is then connected to the transponder 8 via a transponder matching circuit 5 rather than to an antenna. The transponder matches the impedance of the interrogator with its standard 50 ohm antenna matching circuit 4 to the impedance of the transponder. In one embodiment, the transponder matching circuit 5 provides the proper inductance to form a resonant circuit with the on-chip capacitance of the transponder chip. The interrogator chip 3 Error! Reference source not found. and transponder chip function exactly as they would in a standard wireless RFID system. The only functional difference is that there is a physical connection between them rather than the normal electromagnetic one.

Figure 3:
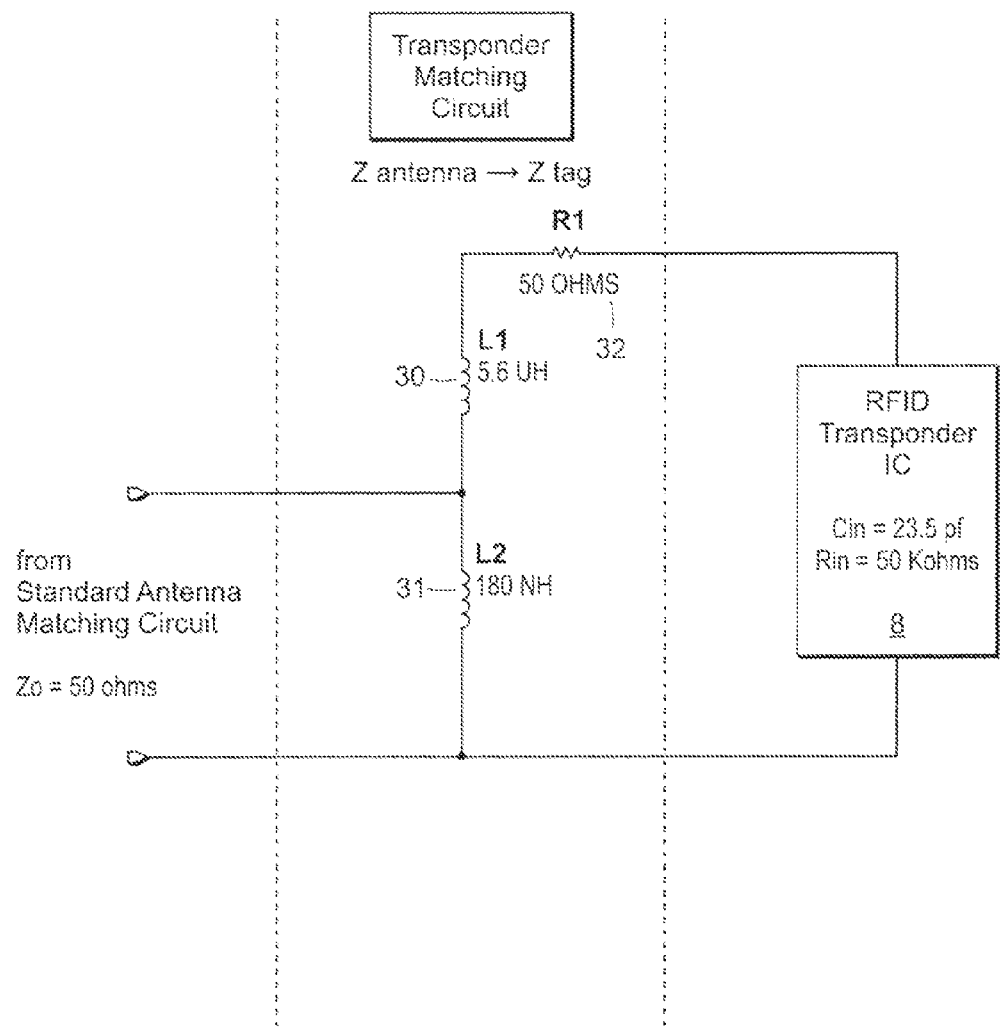
FIG. 3 illustrates in a schematic diagram the matching circuit and IC connections.

In one embodiment, the transponder matching circuit 5 consists of two inductors, L1 30 and L2 31 as sown in FIG. 3. The sum of the two inductors in series with the input capacitance of the Transponder IC 8 forms a parallel resonant circuit.

$$2\Pi f(L1 + L2) = \frac{1}{2\Pi fCin} \quad \text{[Equation 1]}$$

The pair of inductors also provides a voltage divider for impedance matching. To match the impedance of the antenna matching circuit 4 to the impedance of the transponder IC 8, the following equation must be satisfied:

$$\left[\frac{L1+L2}{L1}\right]^2 = \frac{Rin}{Zo} \quad \text{[Equation 2]}$$

where Zo is the output impedance of the antenna matching circuit 4 and Rin is the input resistance of the transponder IC 8.

In one embodiment, the device was constructed to operate at the standard HF frequency of 13.56 MHz. An MLX90121 (NV Melexis SA, Ieper, Belgium) device was used for the interrogator IC 3. An NXP SLI2 ICS20 (NXP Semiconductors Netherlands B.V., Eindhoven, The Netherlands) was used for the transponder IC 8 with a $C_{in}$ of 23.5 pf and a $R_{in}$ of 50 Kohms. With this chip, L1 30 was 5.6 uH and L2 31 was 180 nH. The value of the Q spoiling resistor 32 was 50 ohms. Other values would be used for other embodiments using other devices or implemented at other frequencies. In an alternate embodiment, interrogator chip 3 and transponder chip may operate in any frequency band, with RFID most commonly applied at LF (125 Hz or 134 Hz), HF (13.56 MHz) and UHF (866 MHz-960 MHz). The overall configuration of the system is the same as that for HF, shown in the block diagram in FIG. 3. A benefit to this application is that it would overcome the regulatory issues associated with regional differences in frequency range that defines the UHF band for RFID applications.

When a physical connection is formed between the device (or a component of the device) where the interrogator IC 3 is located and the device (or component of a device) where the transponder IC 8 is located, there is a measurable voltage change at both the antenna matching circuit 4 and at the transponder matching circuit 5. In one embodiment, the primary host system 1 continuously checks via continuous polling for a change in voltage by way of an analog-to-digital converter that is constantly sampling the voltage. An alternate embodiment would use a hardware voltage comparator to sense the change in voltage. When a circuit is connected that draws current from the interrogator, the voltage measured at the transponder matching circuit 5 or the antenna matching circuit 4 will decrease. The value of the voltage drop will be proportional to the current drawn by the Transponder IC 8 and the impedance between the RF generator in the interrogator IC 3 and the place at which the voltage is measured. For instance if the voltage is measured at the antenna matching circuit 4 $V_{antenna\_matching\_circuit}$ is:

$$V_{antenna\_matching\_circuit} = V_{interrogator\_ic} - I_{transponder} Z_{interrogator\_ic} - I_{transponder} Z_{antenna\_matching\_circuit}$$

In this expression, $V_{interrogator\_ic}$ is the voltage across the two contacts of the interrogator IC that are connected to the conductive contacts of the connectable portion, $I_{transponder}$ is the current flowing into and out of the two contacts of the transponder IC and $Z_{interrogator\_IC}$ and $Z_{antenna\_matching\_circuit}$ are the impedances of the interrogator IC and the antenna matching circuit, respectively.

Or if the voltage is measured at the output terminals of the Transponder Matching circuit:

$$V_{transponder\_matching\_circuit} = V_{interrogator\_ic} - I_{transponder} Z_{interrogator\_ic} - I_{transponder} Z_{antenna\_matching\_circuit} - I_{transponder} Z_{transponder\_matching\_circuit}$$

In this expression, $V_{transponder\_matching\_circuit}$ is the voltage across the two input contacts of the transponder matching circuit that are connected to the conductive contacts of the connectable portion and $Z_{transponder\_matching\_circuit}$ is the impedance of the transponder matching circuit.

This voltage change can be used as a means to detect the presence of the transponder. Once the transponder is connected and detected, the nature of communication is exactly as if the transponder were coupled to the interrogator through the other by means of electromagnetic waves. This voltage change can also be used to detect a disconnection.

An alternate means of tag detection is to simply interrogate the device and determine if there is any response. The elements that comprise the primary host system 1 include an RFID interrogator IC 3, electronic components for a standard antenna matching circuit 4 and a transponder matching circuit 5 and may also include a microprocessor 7 to facilitate communication and/or a battery or other form of portable power source residing in the primary host system 1 device itself. In an alternate embodiment wherein the interface cable 20 connects the connectable portion 2 to the primary host system 1, elements that comprise the primary host system 1 are located within the interface cable 20.

In one embodiment, wherein the connectable portion 2 is a "single-use" disposable device, the transponder matching circuit 5 is placed in the connector so as to be close to the transponder but is not placed on the disposable sensor substrate so as to keep cost per use low. The interrogator and the antenna matching circuit 4 are integrated into the cable at the opposing end thus allowing them to have direct contact with the transponder matching circuit 5 and transponder IC 8 through the cable connector 25.

Figure 4:
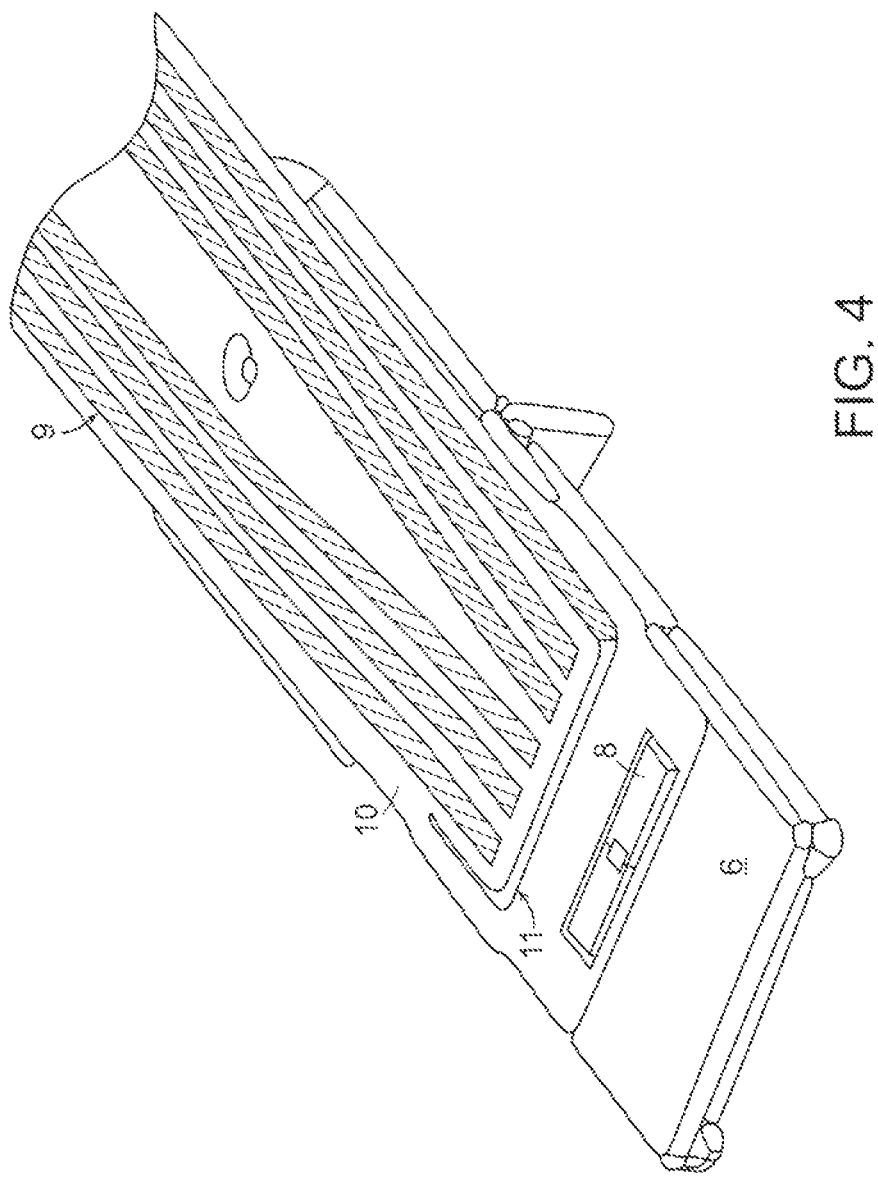
FIG. 4 illustrates one embodiment of the present invention where in the transponder IC is mounted on a flexible substrate with conductive ink traces.
Figure 5:
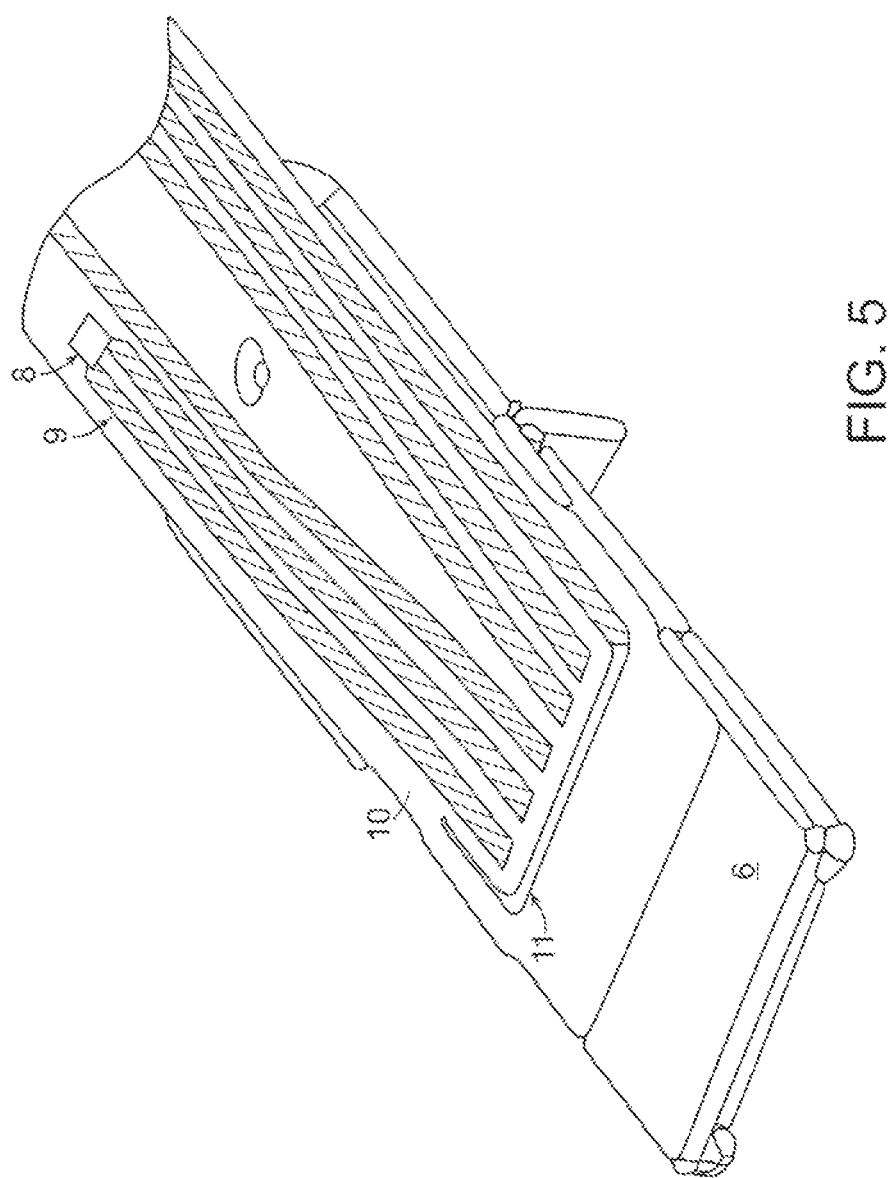
FIG. 5 illustrates an alternate embodiment of the present invention where in the transponder IC is mounted on a flexible substrate and two ink traces are the conductive contacts 9 on which the IC is mounted.

An alternate embodiment is for a connectable portion 2 of the invention to become part of a medical device that is electrically connected to a patient. In one arrangement, shown in FIG. 4, the transponder IC 8 is mounted on a rigid platform 6 on which a flexible substrate 8 is also connected. A series of conductive ink traces 9 carry electrophysiological signals or other data. Upon insertion of the rigid platform into a connector 25 on the interface cable 20 connecting tabs or similar mechanisms form connections with the transponder IC 8 and the conductive traces. Alternately, (FIG. 5) the transponder IC is mounted on a polyester substrate 10 with a series of conductive ink traces, wherein two ink traces are the conductive contacts 9 on which the IC is mounted. The remainder of the conductive ink trances carry electrophysiological signals or may carry other data to interface with the connector 25 on the patient interface cable 20.

In this embodiment the primary host system 1 is also a medical device that would be designed to ensure that leakage currents flowing into a patient are kept at safe limits. In this embodiment the connectable portion 2 carries a ground guard 11 conductor that is utilized by the primary host system 1 to continuously monitor the current flowing into the patient from one or more of the patient connections. This ground guard 11 would serve as a safety monitoring barrier to ensure that no significant level of leakage current is sourced from the RFID transponder IC 8 or its direct connections. If the primary host system 1 were to detect a leakage current that exceeded the safe limits that can flow through the patient ground or other connections, it would shut down the electronics that go to the patient connections and alert the end user that a ground fault condition was detected.

The data on the IC is initially programmed by the manufacturer of the connectable portion 2. It is this preprogrammed data that is read by the interrogator and that is then processed by the microprocessor 7 in the primary host system 1. The programmed data may include information about the device including information pertaining to manufacturing, device configuration or calibration information or personal patient data. This data can be used, for example, to authenticate the source of the device or verify that it meets the necessary conditions for use. Data may include a lot code associated with the event of manufacturing the connectable portion, a connectable portion serial number and a shelf life code. The data may also include an OEM code identifying the distributor of the connectable portion and a usage counter indicating the number of uses remaining for the connectable portion.

Programming data onto the RFID transponder IC 8 in the connectable portion 2 is achieved by direct coupling between a programming system, which contains all the same elements as the primary host system 1, and a transponder IC 8 wherein two pins would compress against the conductive contacts connected to the IC to energize the chip and to program any data into the incorporated memory device.

Employing direct contact between the RFID elements as the method of communication offers improved performance by improving reliability in comparison to similar technologies for achieving the same end goal. The reliability is improved in comparison to a typical smart module memory device due to the reduced number of contact points (two (2) vs. six (6)) which results in fewer contacts that may be damaged during use. Also the connection tolerance associated with two contacts is typically wider than that for 6 contacts. The cost of manufacturing is therefore effectively reduced.

There is a reduced opportunity for electromagnetic interference with the signal in this configuration as opposed to a signal communicated by modulation of an RF electric field as is used conventionally in RFID applications. These benefits combine to offer an increased likelihood of achieving 100% read rates over existing methods. Furthermore, because of the increasing list of applications for RFID technology, the cost for the IC continues to be driven down, and as there is no antenna required for either the reader or the tag, this invention could result in a significant cost reduction.

While the foregoing invention has been described with reference to its preferred embodiments, various alterations and modifications will occur to those skilled in the art. All such alterations and modifications are intended to fall within the scope of the appended claims.

What is claimed:

1. A method of communication with an RFID transponder integrated circuit (IC) comprising:
   interrogating, using a primary host system, an RFID transponder IC through conductive contacts, wherein:
   the interrogating comprises emulating an over-the-air RFID interface; and
   the RFID transponder IC is removably connected to the primary host system through the conductive contacts.

2. The method of claim 1, further comprising detecting the RFID transponder IC.

3. The method of claim 1, further comprising providing power to the RFID transponder IC from the primary host system, wherein the RFID transponder IC is a passive RFID transponder IC.

4. The method of claim 1, further comprising receiving device information from the RFID transponder IC.

5. The method of claim 4, wherein the device information is pre-programmed.

6. The method of claim 1, further comprising monitoring a connection status of a connectable portion including the conductive contacts.

7. The method of claim 6, wherein monitoring comprises monitoring the voltage between the conductive contacts.

8. The method of claim 6, wherein monitoring comprises continuously polling the RFID transponder IC.

9. The method of claim 6, wherein monitoring comprise monitoring using a voltage comparator.

10. The method of claim 1 wherein said primary host system comprises a microprocessor, an interrogator IC, a power source, an antenna matching circuit, and a transponder matching circuit.

11. The method of claim 1, wherein interrogating comprises interrogating using an interface cable that connects a connectable portion including the conductive contacts and the primary host system.

12. The method of claim 1, wherein the primary host system comprises a microprocessor.

13. The method of claim 1, wherein the primary host system comprises an antenna matching circuit.

14. The method of claim 1, wherein the primary host system comprises an interrogator IC.

15. The method of claim 1, wherein the primary host system comprises a transponder matching circuit.

16. The method of claim 1, wherein interrogating comprises communicating between the primary host system and the RFID transponder IC in a frequency band selected from the group consisting of the low frequency (LHF) band, the high frequency (HF) band, and the ultra-high frequency (UHF) band.

17. The method of claim 1, wherein the RFID interrogator IC is coupled to a carrier.

18. The method of claim 17, wherein information related to the carrier is stored as a data string in the RFID transponder IC, and wherein the information is selected from the group consisting of a lot code, a connection portion serial number, a shelf life code, an OEM code identifying the distributor of a connectable portion including the conductive contacts, a usage counter indicating the number of uses remaining, and any combination thereof.

19. The method of claim 17, wherein the carrier contains a ground guard conductor that is utilized by the primary host system to monitor current flow from the conductive contacts to at least one electrical connection to a patient.

20. The method of claim 1, wherein the primary host system comprises an electrophysiological monitor containing at least one electrical connection to a patient.

21. The method of claim 1, wherein the primary host system comprises a medical device and wherein the RFID transponder IC comprises programmed data, including one or more of configuration information, calibration information, and personal patient data, for use by the medical device.

* * * * *